United States Patent [19]

Cortes

[11] Patent Number: 5,120,871

[45] Date of Patent: Jun. 9, 1992

[54] N-[(PENTAALKYL-CYCLOPENTADIENYL)-METHYL]-GLYCINES, PROCESS FOR THE PREPARATION OF THE COMPOUNDS AND THE USE THEREOF IN THE MANUFACTURE OF N-PHOSPHONOMETHYLGLYCINE

[75] Inventor: David A. Cortes, Fairless Hills, Pa.

[73] Assignee: American Cyanamid Company, Stamford, Conn.

[21] Appl. No.: 701,559

[22] Filed: May 16, 1991

[51] Int. Cl.$^5$ ............................................. C01B 25/00
[52] U.S. Cl. ...................................... 562/17; 560/121; 564/189; 558/432
[58] Field of Search ........................ 560/121; 564/189; 558/432; 562/17

[56] References Cited

U.S. PATENT DOCUMENTS

| | | | |
|---|---|---|---|
| 3,799,758 | 3/1974 | Franz | 71/86 |
| 4,053,505 | 10/1977 | Dutra | 260/502.5 |
| 4,237,065 | 12/1980 | Ehrat | 260/502.5 |
| 4,415,503 | 11/1983 | Robbins | 260/502.5 F |
| 4,428,888 | 1/1984 | Robbins | 260/502.5 F |
| 4,946,993 | 8/1990 | Cortes | 562/17 |

FOREIGN PATENT DOCUMENTS 1397111 4/1965 France.

OTHER PUBLICATIONS

Paul A. Grieco et al., J. Am. Chem. Soc., 109:5859–5861.
Bull. Soc. Chim. France, 1962, pp. 1593–1597.

*Primary Examiner*—Arthur C. Prescott
*Assistant Examiner*—Joseph M. Conrad
*Attorney, Agent, or Firm*—Alice C. Brennan

[57] ABSTRACT

This disclosure describes novel compounds, N-[(1,2,3,4,5-pentaalkyl-2,4-cyclopentadien-1-yl)methyl]-glycines, the preparation of the new compounds and their use as intermediates for the preparation of N-phosphonomethylglycine.

10 Claims, No Drawings

N-[(PENTAALKYL-CYCLOPENTADIENYL)METHYL]-GLYCINES, PROCESS FOR THE PREPARATION OF THE COMPOUNDS AND THE USE THEREOF IN THE MANUFACTURE OF N-PHOSPHONOMETHYLGLYCINE

BACKGROUND OF THE INVENTION

1. Field of the Invention

The present invention relates to novel compounds, N-[(1,2,3,4,5-pentaalkyl-2,4-cyclopentadien-1-yl)methyl]-glycines, the preparation of the new compounds and their use as intermediates in the process for the manufacture of N-phosphonomethylglycine.

2. Description of the Related Art

By way of background, U.S. Pat. No. 3,799,758 describes N-phosphonomethylglycine and its use as an important herbicide. N-phosphonomethylglycine and derivatives thereof are effective herbicides at low rates of application when applied postemergence and are biodegradable into harmless residues within a relatively short period of time after their application.

Numerous processes for the preparation of N-phosphonomethylglycine have been disclosed in U.S. Pat. Nos. 4,053,505; 4,237,065; 4,415,503; 4,428,888; 4,946,993 and others. Most of these methods use glycinate esters or phosphinate esters, or both, which necessitate additional materials and reaction steps for their formation.

As reported in the literature, the typical Aza-Diels-Alder reaction between methylglycinate hydrochloride, formaldehyde and cyclopentadiene in water results in azanorbornenes such as the azanorbornene methyl ester described by Paul A. Grieco et al., J. Am. Chem. Soc., 109:5859-5861 (1987). In U.S. Pat. No. 4,946,993, the method to prepare N-phosphonomethylglycine, which involves minimizing the quantity of water in the initial reaction mixture of glycine, formaldehyde and cyclopentadiene and adding the presence of an acid, similarly results in an azanorbornene intermediate.

One major disadvantage to the use of the azanorbornene intermediates in the process to make N-phosphonomethylglycine, however, is the undesirable by-products of the reaction, namely, certain polymeric materials which develop during the procedure. As a consequence of these tar-like substances, tedious purification steps are necessary to obtain the final product in suitable form for use in commercial formulations.

Due to the agronomic importance of N-phosphonomethylglycine, there is a need for improved methods of preparation utilizing new intermediates that are able to form the final product with less reactants and less reaction steps while able to eliminate the undesirable by-products of the azanorbornene reactions.

SUMMARY OF THE INVENTION

It is therefore an important object of the present invention to provide unique intermediate compounds that are able to make N-phosphonomethylglycine with less reaction steps.

Another object is to provide new intermediate compounds that can be made directly into N-phosphonomethylglycine in an integrated process without the isolation of the intermediate compounds.

A further object is to provide a useful method for the manufacture of N-phosphonomethylglycine from key intermediate compounds that eliminate the undesirable by-products of the azanorbornene reactions and simplify the purification of the final product.

Another further object is to provide a process for the preparation of N-phosphonomethylglycine in which one of the starting materials can be recovered and recycled for multiple use.

Further purposes and objects of the present invention will appear as the specification proceeds.

The foregoing objects are accomplished by providing novel intermediate compounds, N-[(1,2,3,4,5-pentaalkyl-2,4-cyclopentadien-1-yl)methyl]-glycines. The background of the invention and its departure from the art will be further described hereinbelow.

DETAILED DESCRIPTION OF THE INVENTION

In accordance with the present invention, the novel compounds, N-[(1,2,3,4,5-pentaalkyl-2,4-cyclopentadien-1-yl)methyl]-glycines, which are useful as key intermediates in a process for the preparation of N-phosphonomethylglycine, are illustrated by formula I:

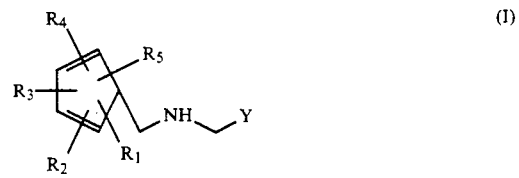

wherein $R_1$, $R_2$, $R_3$, $R_4$ and $R_5$ are $C_1$–$C_4$ alkyl and are the same or different; and Y is $CO_2R_6$, $CONR_7R_8$ or CN wherein $R_6$, $R_7$ and $R_8$ are each independently hydrogen or $C_1$–$C_4$ alkyl.

A particularly preferred compound of formula I is N-[(1,2,3,4,5-pentamethyl-2,4-cyclopentadien-1-yl)methyl]-glycine, methyl ester. Other representative compounds of formula I would include:

N-[(1,2,3,4,5-pentaethyl-2,4-cyclopentadien-1-yl)methyl]-glycine, methyl ester;

N-[(1,2,3,4,5-pentapropyl-2,4-cyclopentadien-1-yl)methyl]-glycine, methyl ester;

N-[(1-methyl, 2-ethyl, 3-methyl, 4-ethyl, 5-methyl-2,4-cyclopentadien-1-yl)methyl]-glycine, methyl ester;

N-[(1,2,3,4,5-pentamethyl-2,4-cyclopentadien-1-yl)methyl]-glycine, ethyl ester;

N-[(1,2,3,4,5-pentamethyl-2,4-cyclopentadien-1-yl)methyl]-glycinonitrile;

N-[(1,2,3,4,5-pentamethyl-2,4-cyclopentadien-1-yl)methyl]-glycinamide;

N-[(1,2,3,4,5-pentamethyl-2,4-cyclopentadien-1-yl)methyl]-glycine;

N-[(1-isopropyl-2,3,4,5-tetramethyl-2,4-cyclopentadien-1yl)methyl]-glycine, methyl ester;

$N^1,N^1$-dimethyl-$N^2$-[(1,2,3,4,5-pentamethyl-2,4-cyclopentadien-1-yl)methyl]-glycinamide; etc.

Generally, the compounds of the present invention may be prepared by reacting a pentaalkylcyclopentadiene of formula II, wherein $R_1$–$R_5$ are as described hereinabove for formula I, an aminomethyl compound of formula III or a salt thereof, wherein Y is as described hereinabove for formula I, and formaldehyde in a $C_1$–$C_4$ alkyl carboxylic acid or a nonacidic solvent in the presence of an acid for a sufficient amount of reaction time at an adequate temperature to yield the intermediates. A reaction sequence is illustrated in Flow Diagram I:

FLOW DIAGRAM I

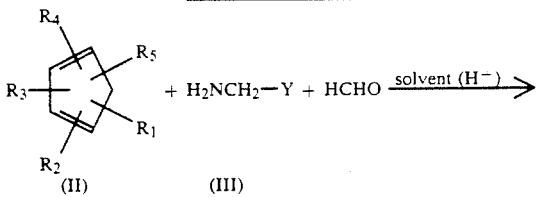

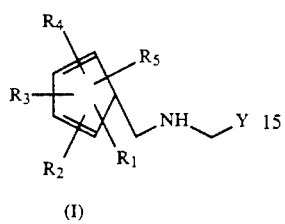

Examples of pentaalkylcyclopentadienes are pentamethylcyclopentadiene, pentaethylcyclopentadiene, etc. This material is employed in amounts ranging from about 0.9 moles to about 5.0 moles, per mole of the compound of formula III, and preferably about 1.0 mole. Examples of the aminomethyl compounds of formula III include glycine, methyl glycinate, ethyl glycinate, isopropyl glycinate, glycinonitrile, glycinamide, etc. Salts of these aminomethyl compounds which are useful in this invention would include, for example, hydrochloride, hydrobromide, hydrogen sulfate and the like.

Any commercially available form of formaldehyde can be employed in the process of the present invention, such as, for example, 37% w/w aqueous formaldehyde; solid paraformaldehyde; a solution of 55% w/w formaldehyde, 35% w/w methanol and 10% w/w water; etc. The typical amount of formaldehyde added to the reaction mixture is about 0.75 moles to about 2.0 moles, per mole of the compound of formula III, with 1.0 mole being preferred. When solid paraformaldehyde is used, the formation of the final product usually depends on the rate of depolymerization of paraformaldehyde. Said rate of depolymerization is increased by decreasing the particle size of the paraformaldehyde or heating the paraformaldehyde with acid before the addition of the aminomethyl compound of formula III.

A particularly preferred $C_1$-$C_4$ alkyl carboxylic acid is glacial acetic acid. Other examples of alkyl carboxylic acids which are useful in the process to make the intermediate compounds would include propionic acid and the like. The usual weight ratio of this solvent, based on the amount of the compound of formula III in the reaction mixture, is from about 1:1 to about 20:1, with about 5:1 being preferred.

Examples of the nonacidic solvents which can be employed in the invention are water, methanol, acetonitrile, toluene and the like. These solvents are present in the reaction mixture in similar weight ratios as mentioned above for the alkyl carboxylic acids. As a general rule, if glycine or a salt of the compounds of formula III is utilized as the starting material in conjunction with a nonacidic solvent, the reaction mixture will not require the incorporation of additional acid. However, when other compounds of formula III such as glycinonitrile are used with the nonacidic solvents, then a certain amount of acid must be added to the reaction mixture. Typical acids useful for this purpose would include the $C_1$-$C_4$ alkyl carboxylic acids such as glacial acetic acid but hydrochloric acid, hydrobromic acid, sulfuric acid and the like would also be beneficial to the reaction.

Contingent upon the total amount of water present in the reaction mixture, the yield of the products will generally vary. When the reaction is carried out with methyl glycinate hydrochloride in an aqueous solvent, the minor product is N-[(1,2,3,4,5-pentamethyl-2,4-cyclopentadien-1-yl)methyl]-glycine, methyl ester, while the major product is a cyclopenta[c]pyrrole-2-acetic acid, methyl ester, for example, the compound of formula IV as shown below, 1,2,3,3a,4,6a-hexahydro-3a,5,6,6a-tetramethyl-4-methylene-cyclopenta]pyrrole-2-acetic acid, methyl ester:

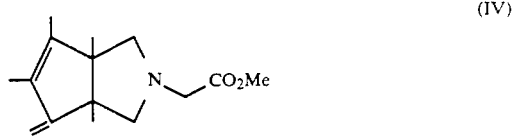

(IV)

However, when the reaction is performed in the presence of a $C_1$-$C_4$ alkyl carboxylic acid, the N-[(cyclopentadien-1-yl)methyl]-glycine is the major product. Desirably, for obtaining a good yield of the latter compound, the total amount of water present in the reaction will be less than about 10% w/w, preferably less than about 5% w/w. To determine the percentage, it is contemplated that the amount of water in the formaldehyde is taken into consideration.

The rate of reaction will, of course, vary in accordance with the temperatures involved during the process. While the reaction can be conducted at a wide range of temperatures, the temperature is typically about 20° C. to about 40° C. resulting in the reaction time to obtain the intermediates at about one-half hour to about twenty-four. Desirably, the reaction time is about five hours to about six hours at a temperature of about 30° C. to about 35° C.

The intermediate compounds of this invention can be separated and/or isolated prior to their use as starting material for the manufacture of the N-phosphonomethylglycine. Isolating the intermediate compounds can be achieved by diluting with water and adjusting the pH with an alkali metal base, such as sodium hydroxide, potassium hydroxide and the like, to greater than or about equal to a pH of 12. During the adjustment of the pH, the temperature of the mixture can be controlled with ice-bath cooling to maintain a temperature of about 30° C. to about 40° C. Then, the reaction mixture can be extracted with an organic solvent such as methylene chloride, chloroform, toluene and the like. If desired, the crude extract can be purified. Examples of suitable purification procedures include any conventional process such as evaporation, crystallization, column chromatography, thin-layer chromatography, fractional distillation, and the like. For an illustration of a typical purification procedure for the preferred compound, N-[(1,2,3,4,5-pentamethyl-2,4-cyclopentadien-1-yl)methyl]-glycine, methyl ester, after the aqueous phase is extracted using the organic solvent, the concentrated organic product can be fractionally distilled under high vacuum at about 115° C. to about 120° C. where the distillate can then be collected at about 120° C. to about 125° C.

The present invention further encompasses a novel method for the preparation of N-phosphonomethylglycine which employs the compounds of formula I as the starting material. As a preferred embodiment, the process for making the intermediate compound is integrated with the process for manufacturing the N-phosphonomethylglycine. Under these circumstances, rather than purifying the intermediate compounds, they are reacted directly with from about 1.0 mole to about 5.0 moles, per mole of the compound of formula III, of a phosphorous compound of formula V:

$$PX_3 \qquad (V)$$

wherein X is halogen; and a $C_1$-$C_4$ alkyl carboxylic acid or an organic solvent in the presence of about 1.0 mole to about 2.0 moles of a hydroxylated compound, followed by adding water and hydrolyzing to obtain the N-phosphonomethylglycine.

Alternatively, the intermediate compounds of formula I can be reacted directly with from about 1.0 mole to about 5.0 moles, per mole of the compound of formula III, of a phosphorous compound of formula VI:

$$P(OR_6)(OR_7)(OR_8) \qquad (VI)$$

wherein $R_6$, $R_7$ and $R_8$ are each independently hydrogen or $C_1$-$C_4$ alkyl; and a $C_1$-$C_4$ alkyl carboxylic acid or an organic solvent, then treating with an aqueous mineral acid such as hydrochloric acid and the like or an aqueous alkali metal base such as sodium hydroxide and the like to obtain the N-phosphonomethylglycine. Optionally, the alkyl carboxylic acid or the organic solvent, whichever is used, can be removed by conventional procedures before treatment with the acid or the base.

The reaction sequence using phosphorous compounds of formulas V and VI is illustrated in Flow Diagram II:

by combining the reaction mixture with water, preferably in the amount of about 1 part to about 5 parts by volume of water, and heating at reflux temperatures.

When the process for making N-phosphonomethylglycine employs isolated, purified compounds of formula I, then they are generally present in the reaction in the range of from about 1.0 mole to about 4.0 moles per mole of the compound of formula I and, desirably, about 2.0 moles.

Examples of suitable phosphorous compounds of formulas V and VI include phosphorous trichloride, phosphorous tribromide, phosphorous acid, dimethyl phosphite, diethyl phosphite, trimethyl phosphite, methylethyl phosphite, etc. A preferred $C_1$-$C_4$ alkyl carboxylic acid is glacial acetic acid, but propionic acid and the like would also be useful in the process of the present invention. Other organic solvents which can be employed in the process would include, for example, aromatic hydrocarbons, halogenated hydrocarbons, lower alkyl alcohols, acetonitrile, etc. The alkyl carboxylic acid or the organic solvent is usually added to the reaction mixture in the weight ratio of about 20:1 to about 3:1, with about 5:1 being preferred. If a phosphorous compound of formula V is used in the presence of a non-hydroxylated solvent, then a stoichiometric amount of a hydroxylated compound such as water or methanol is required.

The rate of the reaction to prepare the N-phosphonomethylglycine depends, of course, on the temperature at which the reaction proceeds in the particular solvent that is used. The process takes place at a wide range of temperatures but typically at a temperature of about 50° C. to about 110° C. for a sufficient amount of reaction time, which is usually between about four hours to about twelve hours. Preferably, the temperature is maintained at about 80° C. to about 90° C. for the

FLOW DIAGRAM II

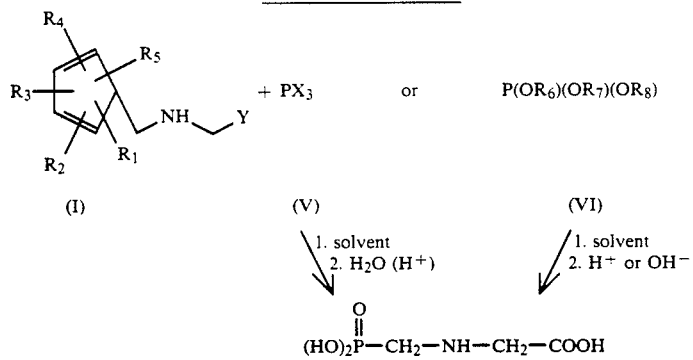

If a phosphorous compound of formula V is used in the presence of a $C_1$-$C_4$ alkyl carboxylic acid, the initial major product of the reaction is an amide derived from the corresponding carboxylic acid. For example, if $PX_3$ is used with glacial acetic acid in a preferred embodiment of the invention, the major product of the reaction is an N-acetylated intermediate compound of formula VII as shown below:

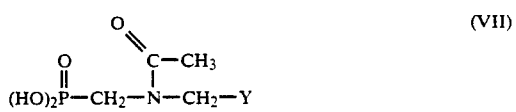

The intermediate amide compound is subsequently hydrolyzed, as illustrated in the above Flow Diagram II, reaction to run about five hours to about six hours. Obviously, using the lower temperatures will increase the time needed to complete the reaction. The hydrolysis step is conveniently conducted for about twenty-six hours to about thirty hours at a refluxing temperature of about 90° C. to about 110° C., preferably at about 98° C., but the time can be easily varied by the temperature. It is clear that the hydrolysis can be done at less time with higher temperatures or, conversely, although less practical, it can take more time at lower temperatures.

Whether phosphorous compounds of formula V or VI are employed, isolation of the final product N-phosphonomethylglycine as a solid from the hydrolysis reaction may be achieved by concentrating the reaction mixture in vacuo, adjusting the pH to about 1.3 to about 1.5 to precipitate the desired product and subsequently collecting the N-phosphonomethylglycine by filtration.

Advantageously and surprisingly, using the N-[(cyclopentadienyl)methyl]-glycines of formula I in the manufacture of N-phosphonomethylglycine provides a profound departure from the state of the art. The benefit of these novel precursors of N-phosphonomethylglycine over the prior intermediates such as the azanorbornenes is that the pentaalkylcyclopentadiene can be recovered and recycled for mutliple use. Conventional recovery and recycling techniques which are well known in the art can be employed with the process of this invention. Moreover, a further benefit of the N-[(cyclopentadienyl)methyl]-glycines of the present invention over the art is that the new intermediates do not generate the undesirable by-products of the art processes. Without developing the polymeric or tar-like substances during the manufacture of N-phosphonomethylglycine, the purification of the final product is easier and more efficiently performed than heretofore possible.

It should be appreciated that when typical reaction conditions (e.g., temperatures, mole ratios, reaction times) have been hereindescribed, the conditions that are either above or below the specified range can also be used, though generally less favorably. While preferred reactants have been identified herein, it is contemplated that the present invention would include chemical equivalents to each reactant specifically enumerated in this disclosure. Also, as used herein, the term "percent" or "%" refers to weight percent and the terms "mole" or "moles" refer to gram moles.

A further understanding of the present invention can be obtained from the following examples. However, the examples are set forth only for the illustration of certain aspects of the invention and are not to be construed as limitations thereon. Unless otherwise expressed, all parts are by weight.

EXAMPLE 1

Preparation of
N-[(1,2,3,4,5-pentamethyl-2,4-cyclopentadien-1-yl)methyl]-glycine, Methyl Ester To a stirred mixture of methyl glycinate hydrochloride (6.28 g, 0.05 mole) in 30 mL of glacial acetic acid and 37% aqueous formaldehyde (4.1 g, 1.5 g real, 0.05 mole) is added pentamethylcyclopentadiene (6.81 g, 0.05 mole) after all of the solid methyl glycinate has dissolved. A light brown solution is initially obtained. The temperature is kept at 35° C. for five minutes with ice-bath cooling to control the exotherm. The color of the solution changes to light purple and the temperature is then kept at 33° C. for about 6 hours. This reaction mixture is combined with 100 mL of water and the aqueous phase is extracted with two×20 mL portions of methylene chloride. The clear aqueous phase is then treated with 50% sodium hydroxide, with cooling to maintain a temperature of 35° C., to pH 12. The basic aqueous phase is extracted with two×30 mL portions of methylene chloride. The organic layer is concentrated in vacuo to give approximately 5.0 g of the title compound. Yield is 40%, about 80% purity, of the product which is identified by proton nuclear magnetic resonance, carbon-13 nuclear magnetic resonance and electron impact mass spectral analyses.

EXAMPLE 2

Preparation of
N-[(1,2,3,4,5-pentamethyl-2,4-cyclopentadien-1-yl)methyl]-glycinonitrile To a stirred mixture of glycinonitrile hydrochloride (1.85 g, 0.020 mole) in 10 mL of glacial acetic acid and 37% aqueous formaldehyde (1.80 g, 0.66 g real, 0.022 mole) is added pentamethylcyclopentadiene (3.0 g, 0.022 mole). The reaction is stirred at about 25° C. to about 30° C. overnight. The reaction mixture is combined with 50 mL of water and then treated with 50% sodium hydroxide until the pH is raised to 12. The basic aqueous phase is extracted with two×20 mL portions of methylene chloride. The organic layer is concentrated in vacuo to give the title compound.

EXAMPLE 3

Preparation of N-phoshonomethylglycine Via an Intermediate Compound
N-[(1,2,3,4,5-pentamethyl-2,4-cyclopentadien-1-yl)methyl]-glycine, Methyl Ester To a stirred mixture of the compound prepared in Example 1 (0.474 g, 2.0 mmole) in 10 mL of glacial acetic acid is added phosphorous trichloride (0.55 g, 4.0 mmole). The reaction mixture is heated to about 80° C. to about 90° C. for about 5 hours. Then, the mixture is cooled to 25° C. and combined with 50 mL of water. The aqueous phase is extracted with two×25 mL portions of methylene chloride, followed by refluxing at about 90° C. to about 98° C. for about 27 hours. Cooling to 25° C. and concentration in vacuo of the reaction mixture gives approximately 10.2 g of solution, which is assayed to be 1.1% w/w of N-phosphonomethylglycine by high pressure liquid chromatography, 33.0% yield. Concentration to dryness gives a residue which is shown by proton and carbon-13 nuclear magnetic resonance spectral analyses to contain N-phosphonomethylglycine.

EXAMPLE 4

Preparation of N-phosphonomethylglycine Via an Intermediate Compound,
N-[(1,2,3,4,5-pentamethyl-2,4-cyclopentadien-1-yl)methyl]-glycine, Methyl Ester Using an Integrated Procedure To 10 mL of glacial acetic acid is added paraformaldehyde (0.75 g, 0.025 mole). The mixture is heated to about 80° C. to about 85° C. for about 1 hour to dissolve the paraformaldehyde. The reaction is then cooled to 30° C. and glycine (1.5 g, 0.020 mole) is added, followed by pentamethylcyclopentadiene (3.0 g, 0.022 mole). The reaction is stirred at about 30° C. to about 35° C. overnight and then phosphorous trichloride (4.1 g, 0.030 mole) is added while the temperature is maintained below 70° C. The reaction mixture is heated to about 80° C. to about 90° C. for about 6 hours. Then, the mixture is cooled to 25° C. and combined with 50 mL of water. The reaction is refluxed for 24 hours to produce a solution of N-phosphonomethylglycine.

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

I claim:

1. A method for the preparation of N-phosphonomethylglycine which comprises reacting a compound having the structure:

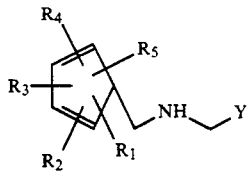   (I)

wherein $R_1$, $R_2$, $R_3$, $R_4$ and $R_5$ are $C_1$–$C_4$ alkyl and are the same or different; and Y is $CO_2R_6$, $CONR_7R_8$ or CN wherein $R_6$, $R_7$ and $R_8$ are each independently hydrogen or $C_1$–$C_4$ alkyl; with from about 1.0 mole to about 5.0 moles of a phosphorous compound of formula V:

$$PX_3 \qquad (V)$$

wherein X is halogen; and a $C_1$–$C_4$ alkyl carboxylic acid or an organic solvent in the presence of about 1.0 mole to about 2.0 moles of a hydroxylated compound, at a temperature of about 50° C. to about 110° C. for a sufficient amount of reaction time, then adding water and hydrolyzing to obtain the N-phosphonomethylglycine.

2. The method according to claim 1, wherein the hydrolysis step is conducted for about twenty-six to about thirty hours at a temperature of about 90° C. to about 110° C.

3. The method according to claim 1, wherein the phosphorous compound is phosphorous trichloride or phosphorous tribromide.

4. The method according to claim 1, wherein the hydroxylated compound is water or methanol.

5. A method for the preparation of N-phosphonomethylglycine which comprises reacting a compound having the structure:

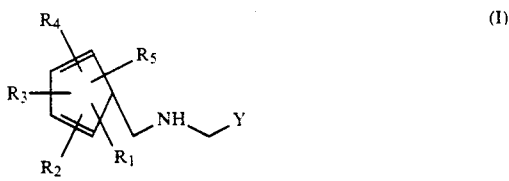   (I)

wherein $R_1$, $R_2$, $R_3$, $R_4$ and $R_5$ are $C_1$–$C_4$ alkyl and are the same or different; and Y is $CO_2R_6$, $CONR_7R_8$ or CN wherein $R_6$, $R_7$ and $R_8$ are each independently hydrogen or $C_1$–$C_4$ alkyl; with from about 1.0 mole to about 5.0 moles of a phosphorous compound of formula VI:

$$P(OR_6)(OR_7)(OR_8) \qquad (VI)$$

wherein $R_6$, $R_7$ and $R_8$ are as described hereinabove; and a $C_1$–$C_4$ alkyl carboxylic acid or an organic solvent, at a temperature of about 50° C. to about 110° C. for a sufficient amount of reaction time, then treating with an aqueous mineral acid or an aqueous alkali metal base to obtain the N-phosphonomethylglycine.

6. The method according to claim 5, wherein the phosphorous compound is dimethyl phosphite, diethyl phosphite, trimethyl phosphite, phosphorous acid or methylethyl phosphite.

7. The method according to claim 1 or 5, wherein the reaction time is about five hours to about six hours at a temperature of about 80° C. to about 90° C.

8. The method according to claim 1 or 5, wherein the compound of formula I is N-[(1,2,3,4,5-pentamethyl-2,4-cyclopentadien-1-yl)methyl]-glycine, methyl ester.

9. The method according to claim 1 or 5, wherein the $C_1$–$C_4$ alkyl carboxylic acid is glacial acetic acid or propionic acid.

10. The method according to claim 1 or 5, wherein the pentaalkylcyclopentadiene is recovered and recycled for multiple use.

* * * * *